(12) United States Patent
Velayutham

(10) Patent No.: US 10,598,605 B2
(45) Date of Patent: Mar. 24, 2020

(54) AUTOMATED TABLET TOOLING INSPECTION SYSTEM AND A METHOD THEREOF

(71) Applicant: PACIFIC TOOLS PVT. LTD., Porur, Chennai (IN)

(72) Inventor: N. Velayutham, Porur (IN)

(73) Assignee: PACIFIC TOOLS PVT. LTD. (IN)

( * ) Notice: Subject to any disclaimer, the term of this patent is extended or adjusted under 35 U.S.C. 154(b) by 162 days.

(21) Appl. No.: 15/803,178

(22) Filed: Nov. 3, 2017

(65) Prior Publication Data
US 2018/0328858 A1    Nov. 15, 2018

(51) Int. Cl.
| | | |
|---|---|---|
| *G01B 11/14* | (2006.01) | |
| *G01N 21/95* | (2006.01) | |
| *G01B 11/02* | (2006.01) | |
| *B30B 15/02* | (2006.01) | |
| *B30B 15/06* | (2006.01) | |
| *G01B 11/24* | (2006.01) | |
| *G01B 11/08* | (2006.01) | |
| *B30B 11/08* | (2006.01) | |

(52) U.S. Cl.
CPC ............. *G01N 21/95* (2013.01); *B30B 11/08* (2013.01); *B30B 15/02* (2013.01); *B30B 15/065* (2013.01); *G01B 11/02* (2013.01); *G01B 11/08* (2013.01); *G01B 11/2433* (2013.01); *G01N 21/9508* (2013.01)

(58) Field of Classification Search
CPC ..... G06F 3/0482; H04M 19/04; H04M 1/247; H04M 1/2471; H04M 1/2477; H04M 1/72519; H04M 2203/254; H04M 2250/74; H04M 3/493; B30B 11/08; B30B 15/02; B30B 15/065; G01B 11/02; G01B 11/08; G01B 11/2433; G01N 21/95
USPC .......................................................... 356/301
See application file for complete search history.

(56) References Cited

U.S. PATENT DOCUMENTS 5,768,138 A     6/1998   Ruotolo
2010/0294927 A1*  11/2010  Nelson ................. A61K 9/2072
                                                            250/307

OTHER PUBLICATIONS

Tooling Inspection and Analysis System by Bosch; May 2015; 1 page.

* cited by examiner

*Primary Examiner* — Sunghee Y Gray
(74) *Attorney, Agent, or Firm* — Barnes & Thornburg LLP

(57) ABSTRACT

An automated tablet tooling inspection system (100) for inspecting defects in tablet tooling's including upper punch, lower punch and die. The system (100) comprising of a base plate (101), a punch holder (102), a punch stopper (103), a die holder (104), a LM rail and carriage assembly (105), a LED Micrometer (107) to measure parameters of said tablet tooling, a Laser sensor or con focal sensor (108) to measure parameters of said tablet tooling and a control unit. The automated tooling inspection and system (100) reduces the inspection time of said tablet tooling by minimizing manual intervention; wherein said manual intervention is reduced by eliminating the requirement of changing configuration of said system (100) when a different type of tablet tooling is inspected such as TSM/Euro, B, D, BD, BB and BBS and the like.

7 Claims, 10 Drawing Sheets

AUTOMATED TABLET TOOLING INSPECTION SYSTEM AND A METHOD THEREOF

FIELD

The present disclosure relates to an automated inspection system, more particularly, an automated system and method thereof for inspecting tools used in pharmaceutical manufacturing processes such as tablet tooling with reduced inspection time and enhanced accuracy.

BACKGROUND

Tablet press systems/tablet tooling also referred as compressing machines in the pharmaceuticals industry are mechanical devices that compress powder into tablets of uniform size and weight. A tablet press can be used to manufacture tablets of a wide variety of sizes and materials, including pharmaceuticals, drugs, cleaning products, and cosmetics.

To form a tablet, the formulation material must be metered into a cavity formed by two punches and a die, and then the punches must be pressed together with great force to fuse the material together. The upper and lower punches along with the die are referred to as a tooling assembly. In the first step of a typical operation, the bottom punch is lowered in the die creating a cavity into which the granulated feedstock is fed. The exact depth of the lower punch can be precisely controlled to meter the amount of powder that fills the cavity. The excess is scraped from the top of the die, and the lower punch is drawn down and temporarily covered to prevent spillage. Then, the upper punch is brought down into contact with the powder as the cover is removed. The force of compression is delivered by high pressure compression rolls which fuse the granulated material together into a hard tablet. After compression, the lower punch is raised to eject the tablet. Therefore, it is of critical importance that said punches and die have accurate dimensions, as faulty punches and die can result in unsatisfactory products which are not within the preset standards.

Many systems exist in the art that facilitates inspection of tools used in pharmaceuticals industry, such as punches and dies of the tablet tooling. In such systems, analysis is performed for identifying defects and/or suspected defects in the measurement of a tooling assembly. Generally, these higher order analyses occur after initial analysis/operations that serve to identify defects/suspected defects, and can comprise more sophisticated analysis that can provide better inspection results.

One such system has been disclosed in U.S. Pat. No. 5,768,138 A. The specification discloses a method for inspecting a tool used in a tableting punch and an apparatus for performing the method. The tool is clamped into a holder which positions it under an imaging device which captures an image of a top of the tool. Based on the captured image, an angular position of the tool is rotated so the tool has a predetermined angle. After the tool is rotated, an image of a profile of a tip of the tool is captured so that the radius of the tip of the tool can be determined.

The level of accuracy in the disclosed system is comparatively less, as it based on vision measurement and evaluates parameters such as working length of a punch on basis of relative measurements for e.g. by measuring cup depth of the punch based on radius of concavity of said punch and subtracting it from overall length to calculate the working length of said punch.

Punches and dies can be of different types. The inspection systems of the prior art require changes in the configuration every time when a different type of tablet tooling system is to be inspected. This leads to manual intervention as generally gauges or masters are required to setting up the fixture. One such system in the prior art is Tooling Inspection and Analysis System by Bosch (hereinafter referred as Bosch system) that is capable of inspecting different types of punches and dies but with the requirement of setting tools whenever a different type of punch or die is to be inspected, thereby increasing the time of inspection and leading to a much higher degree of manual intervention.

Further, the Bosch system has different fixtures to measure different parameters of the tool to be inspected resulting in a further increase of time and manual intervention.

Thus to solve above and other problems there is a requirement of a system that provides an automated inspection of various tablet tooling based on multiple parameters with reduced inspection time and enhanced accuracy.

OBJECTIVES

Accordingly an object of the present disclosure is to overcome the drawbacks of the prior art. Another object of the present disclosure is to provide an automated tablet tooling inspection system and a method thereof to reduce inspection time. Another object of the present disclosure is to provide an automated tablet tooling inspection system and a method thereof with enhanced accuracy of inspection. Yet another object of the present disclosure is to provide an automated tablet tooling inspection system and a method thereof to minimize manual intervention during the inspection process. Yet another object of the present disclosure is to provide an automated tablet tooling inspection system that is easy to operate without any specific skill requirements for the operator/user.

SUMMARY

The present disclosure provides an automated tablet tooling system and a method thereof to reduce the inspection time of tablet tooling by reducing the manual intervention along with enhanced accuracy of inspection, wherein said system inspects the defects in the dimensions of a tablet tooling including an upper punch, a lower punch and a die.

The various parameters which may be measured by said system includes but not limited to punch barrel diameter, punch tip size maximum, punch tip size minimum, punch barrel to tip concentricity, punch overall length, punch working length, punch tip cup depth, die outer dimension and die height.

In accordance with an embodiment, an automated tablet tooling inspection system for inspecting defects in tablet tooling including an upper punch, a lower punch and a die comprises:

a base plate;
a punch holder and a punch stopper adapted to hold punches, said punch holder fixed with said base plate;
a die holder adapted to hold dies, said die holder fixed with said base plate;
a LED micrometer fixed with a LM rail and carriage assembly to measure parameters of said tablet tooling, wherein said LM rail and carriage assembly fixed with said base plate;
a Laser sensor or con focal sensor fixed with said base plate to measure parameters of said tablet tooling;

a control unit comprising of a Graphical User Interface and a storage device adapted to receive instructions from an operator for initialing the process of inspecting defects in said tablet tooling, said initiation comprises sending commands to LED micrometer and Laser sensor or con focal sensor to inspect said parameters of said tablet tooling and storing said parameters along with a pass/fail status in the storage device as a report wherein said automated tablet tooling inspection system reduces the inspection time of said tablet tooling by minimizing manual intervention.

In accordance with said embodiment, said manual intervention is reduced by eliminating the requirement of changing configuration of said automated tooling inspection system when a different type of tablet tooling is inspected such as TSM/Euro, B, D, BD, BB and BBS and the like.

In accordance with said embodiment, said LED micrometer measures parameter not limited to punch barrel diameter, punch tip dimension, punch barrel to tip concentricity and die outer diameter.

In accordance with said embodiment, said Laser sensor or con focal sensor measure parameters not limited to punch overall length, punch working length, punch cup depth and die height.

In accordance with said embodiment, said punch barrel to tip concentricity is measured in one single cycle along with the punch working length without any requirement of change in said system configuration thereby further reducing the inspection time.

In accordance with said embodiment, said storage device can be selected from a group of primary storage device, such as RAM, or a secondary storage device, such as a hard drive; wherein said secondary storage can be removable, internal, or external storage.

In accordance with said embodiment, said report comprises of said parameters inspected and a pass and fail status; wherein said pass/fail status is determined on the basis of a predetermined tolerance limit, if parameters inspected are within the predetermined tolerance limit the status is stored as pass or else fail.

In accordance with another embodiment of the present disclosure there is provided a method to inspect defects in a punch of a tablet tooling in an automated tablet tooling inspection system, said system comprises of a base plate, a punch holder, a punch stopper, a LM rail and carriage assembly, a LED Micrometer, a Laser sensor or con focal sensor and a control unit comprising of a Graphical User Interface and a storage device; and said method comprising the steps of:

placing the punch in the punch holder of the automated tablet tooling inspection system, said punch is placed with tip facing the laser sensor or con focal sensor of the system, and head touching the punch stopper of the automated tooling inspection system;

initiating inspection of said punch by an operator through the graphical user interface of the control unit by sending commands to said LED micrometer and Laser sensor or con focal sensor to measure parameters;

LED Micrometer measures parameter of the punch not limiting to punch barrel diameter 1, punch barrel diameter 2, punch barrel to tip concentricity, punch tip dimensions and punch working length;

the automated tooling inspection system prompts the operator through audio/visual message on the graphical user interface of the control unit to change the punch position; wherein according to the changed position the head of the punch should face the Laser sensor or con focal sensor;

Laser sensor or con focal sensor of the automated tablet tooling inspection system measures parameters of the punch not limiting to punch overall length, punch working length and punch cup depth;

storing said parameters measured by LED Micrometer and Laser sensor or con focal sensor in the storage device of the control unit a report including said parameter measured along with a pass or fail status, wherein said report can be viewed on the graphical user interface of said control unit;

repeating the above steps of inspecting for inspecting another punch.

BRIEF DESCRIPTION OF THE DRAWINGS

The following drawings are illustrative of preferred embodiment for enabling the present disclosure, are descriptive of some methods, and are not intended to limit the scope of the invention. The drawings are not to scale (unless so stated) and are intended for use in conjunction with the explanations in the following detailed description.

DETAILED DESCRIPTION

Figure 1:
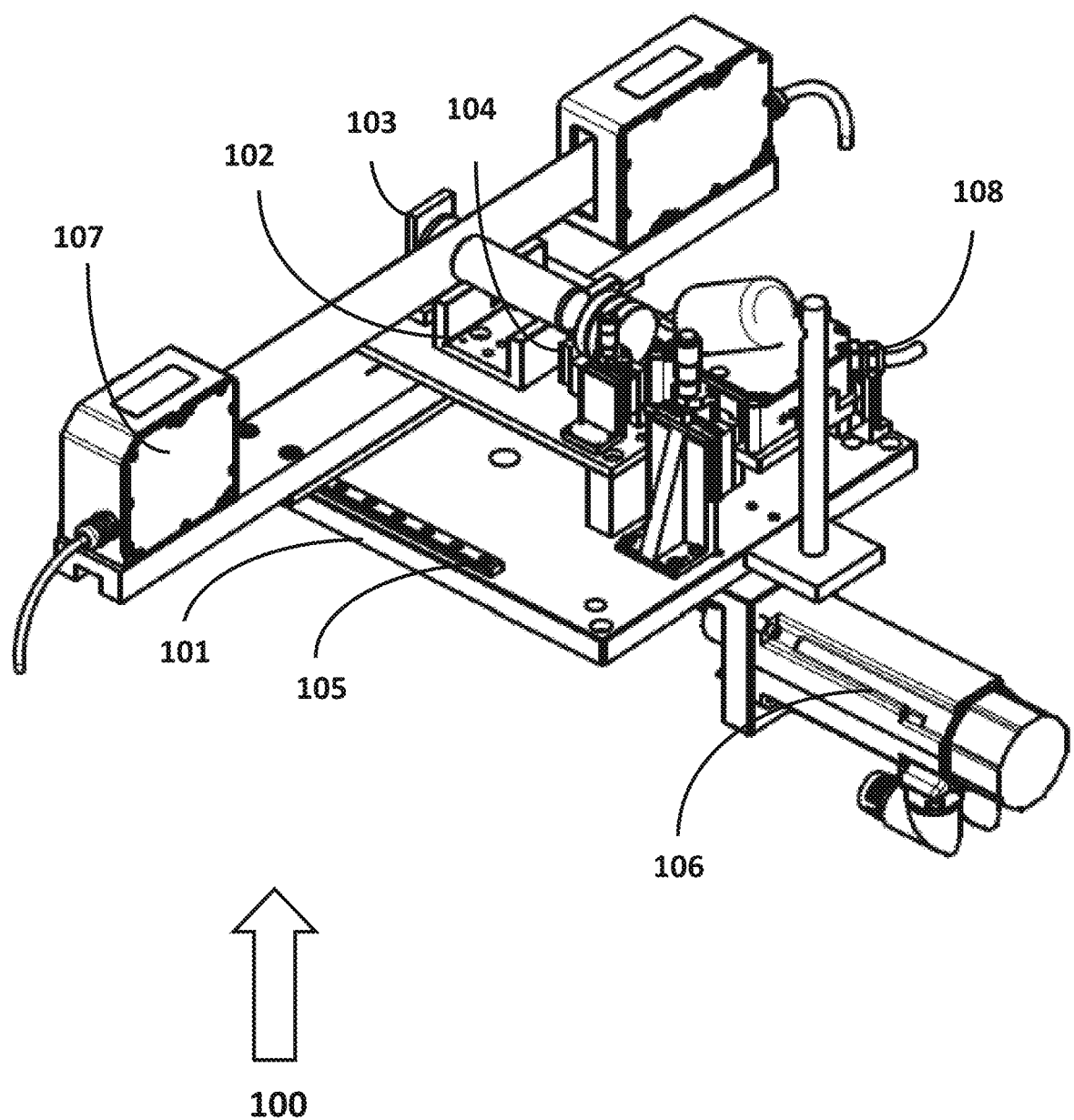
FIG. 1: shows a perspective view of the automated tablet tooling inspection system according to the present disclosure.

The preferred embodiments of the disclosed subject matter are described in more detail hereinafter with reference to the accompanying drawings. The disclosed subject matter may, however, be embodied in many different forms and should not be construed as limited to the exemplary embodiments set forth herein. Rather, the exemplary embodiments are provided so that this disclosure is thorough and complete, and will convey the scope of the disclosed subject matter to those skilled in the art. Like reference numerals in the drawings denote like elements.

It is to be noted that, as used in the specification and the appended claims, the singular forms "a", "an" and "the" include plural referents unless the context clearly dictates otherwise. It should also be noted that the term "or" is generally employed in its sense including "and/or", unless the content clearly dictates otherwise. It should also be noted that by the term "substantially" it is meant that the recited characteristic, parameter, or value need not be achieved exactly, but that deviations or variations, including for example, tolerances, measurement error, measurement accuracy limitations and other factors known to those skilled in the art, may occur in amounts that do not preclude the effect the characteristic was intended to provide.

Hereinafter, an automated tablet tooling inspection system will be explained in more details. The same reference numerals are given to the same parts as those of the aforementioned embodiments and their minute explanation has been omitted.

Figure 2:
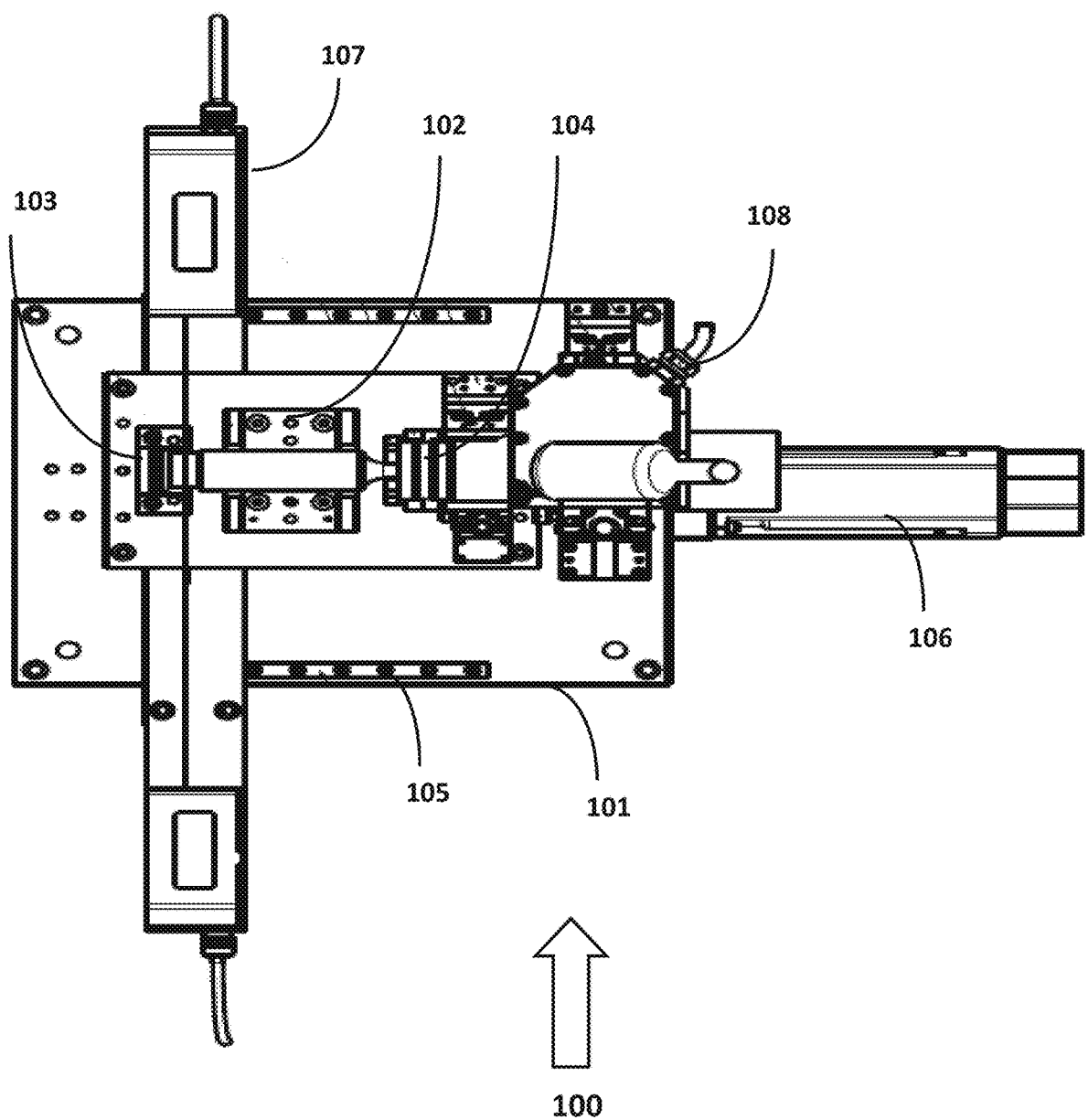
FIG. 2: shows a top view of the automated tablet tooling inspection system according to the present disclosure.
Figure 3:
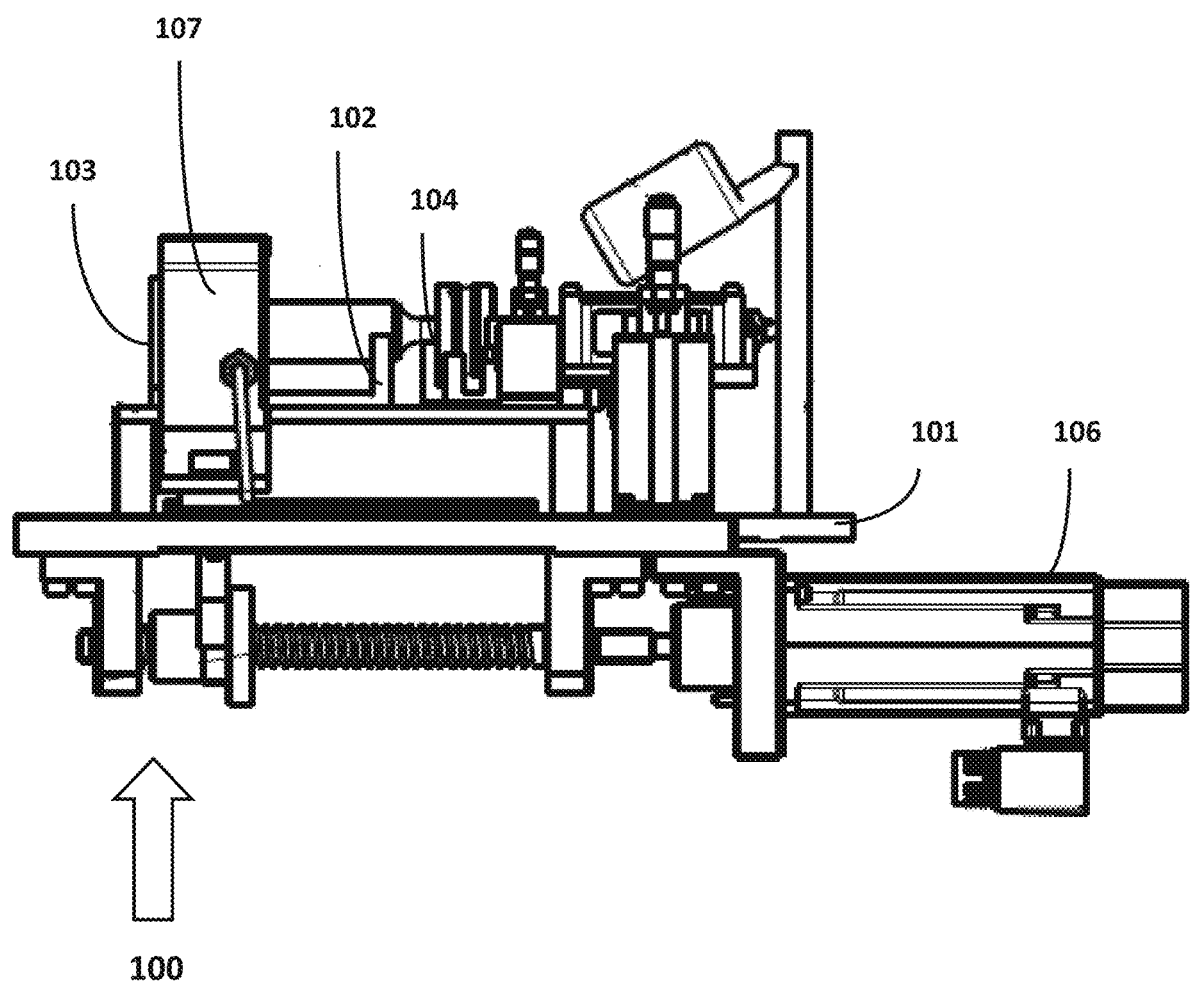
FIG. 3: shows a side view of the automated tablet tooling inspection system according to the present disclosure.

Referring to FIGS. 1, 2 and 3 a perspective, top and side view of an automated tablet tooling inspection system (100) according to an embodiment of the present disclosure for inspecting defects in tablet tooling. The automated tablet tooling inspection system (100) comprises of a base plate (101), a punch holder (102), a punch stopper (103), a die holder (104), a LM rail & carriage assembly (105), a servo motor (106), a LED Micrometer (107) and a Laser sensor or con focal sensor (108) and a control unit (not shown).

The automated tablet tooling inspection system (100) reduces the inspection time of tablet tooling by reducing the manual intervention along with enhanced accuracy of inspection, wherein said system (100) inspects the defects in the dimensions of a tablet tooling including an upper punch, a lower punch and a die. The manual intervention is reduced by eliminating the requirement of changing configuration of said automated tablet tooling inspection system (100) when a different type of tablet tooling is inspected such as TSM/Euro, B, D, BD, BB and BBS and the like.

The base plate of the automated tooling inspection system (100) can be of any suitable material. The punch holder (102) and punch stopper (103) of the automated tooling inspection system (100) is adapted to hold punches of tablet tooling. The die holder (104) of the automated tablet tooling inspection system (100) is adapted to hold dies of tablet tooling to be inspected.

The LED micrometer (107) is fixed on a LM rail and carriage assembly (105) which is fixed to the base plate (101). LM rail and carriage assembly (105) of the automated tooling inspection system (100) facilitates to and fro movement of the LED micrometer (107) parallel to said punch holder (102). The servo motor (106) facilitates movement and positioning of the LED Micrometer (107). The LED Micrometer (107) of the automated tablet tooling inspection system (100) measures parameter not limited to punch barrel diameter, punch tip dimension, punch barrel to tip concentricity and die outer diameter.

The Laser sensor or con focal sensor (108) fixed with said base plate (101) to measure parameters not limited to punch overall length, punch working length, punch cup depth and die height of said tablet tooling. The system (100) inspects punch barrel to tip concentricity in one single cycle along with the punch working length without any requirement of change in said system (100) configuration thereby further reducing the inspection time.

The control unit of the automated tooling inspection system (100) comprising of a Graphical User Interface and a storage device adapted to receive instructions from an operator for initialing the process of inspecting defects in said tablet tooling, said initiation comprises sending commands to LED micrometer and Laser sensor or con focal sensor to measure said parameters of said tablet tooling and storing said parameters along with a pass/fail status in the storage device as a report; wherein said pass/fail status is determined on the basis of a predetermined tolerance limit, if parameters are within the predetermined tolerance limit the status is stored as pass or else fail. The tolerance limit according to said embodiment is within 0.001 mm; thereby providing an accurate report. The storage device can be selected from a group of primary storage device, such as RAM, or a secondary storage device, such as a hard drive; wherein said secondary storage can be removable, internal, or external storage. The control unit may be selected from a group consisting of multiprocessors, microprocessors, microcontroller or other like devices capable of executing instructions.

Optionally, the tablet tooling inspection system (100) may further comprise a tool (not shown) such as a matrix reader for reading serial numbers engraved in punches and dies to be inspected. The tool facilitates reading, verifying and storing the serial number in the report. Storing the serial number in the report of a punch/die facilitates the user to track the wear trend of a punch/die on successive inspection of the punch/die.

Figure 4A:
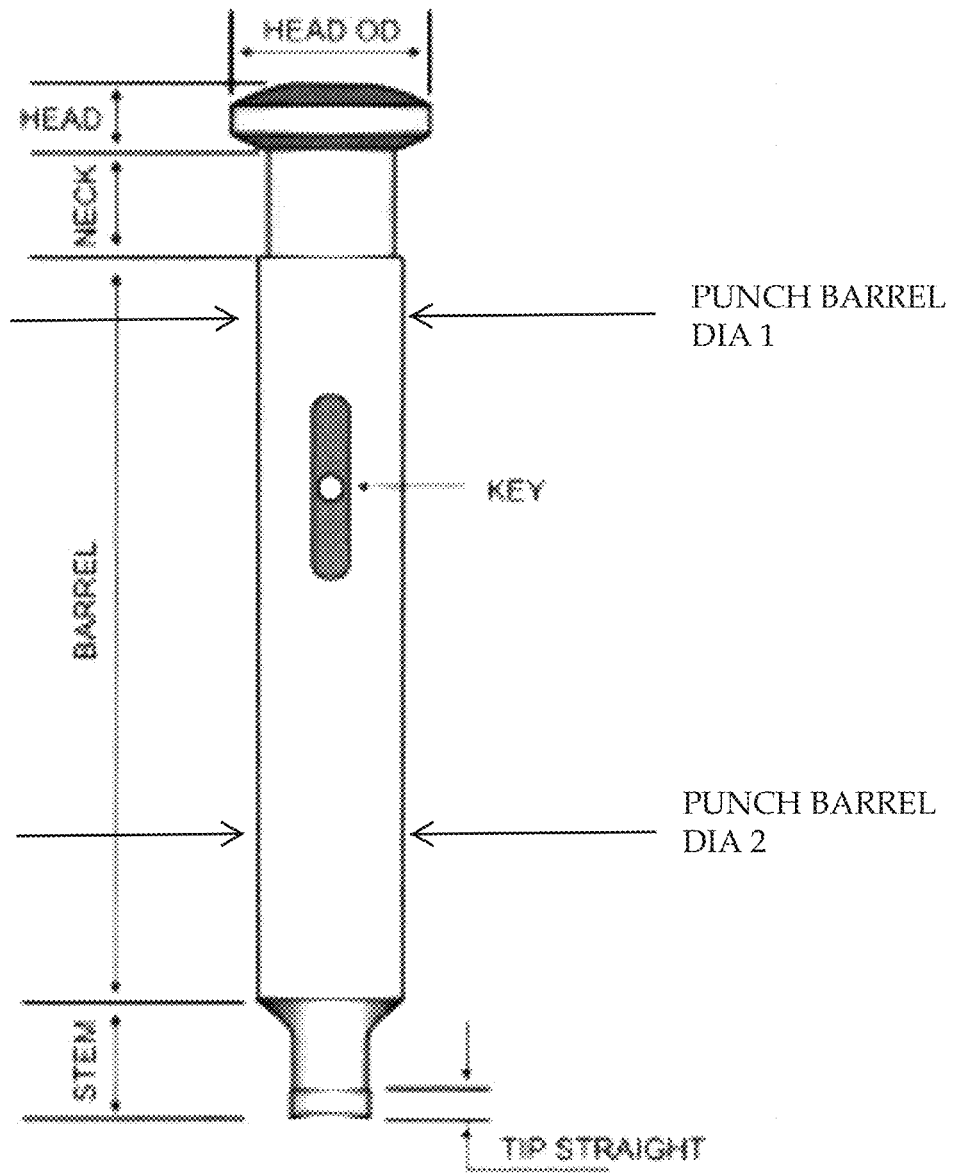
FIGS. 4(*a*) and 4(*b*): illustrates an exemplary punch along with various parameters to be inspected by the automated tablet tooling inspection system according to an embodiment of the present disclosure.
Figure 4B:
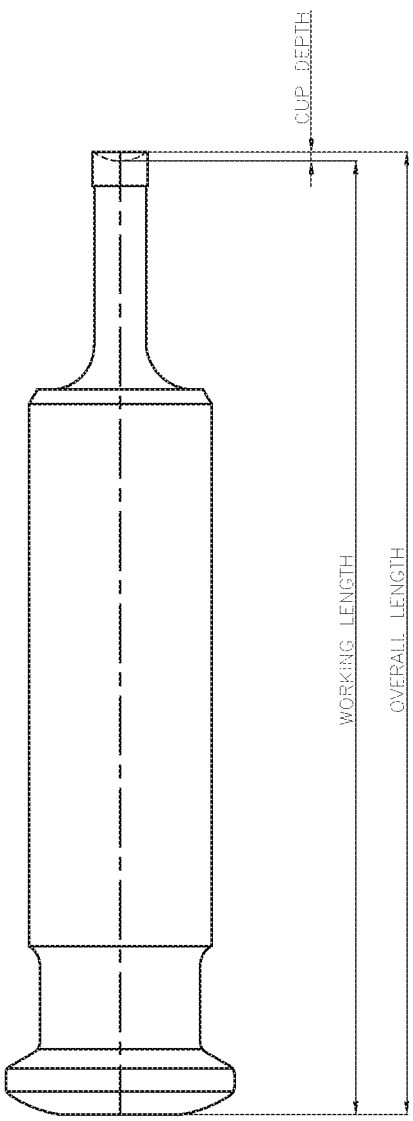
Figure 5:
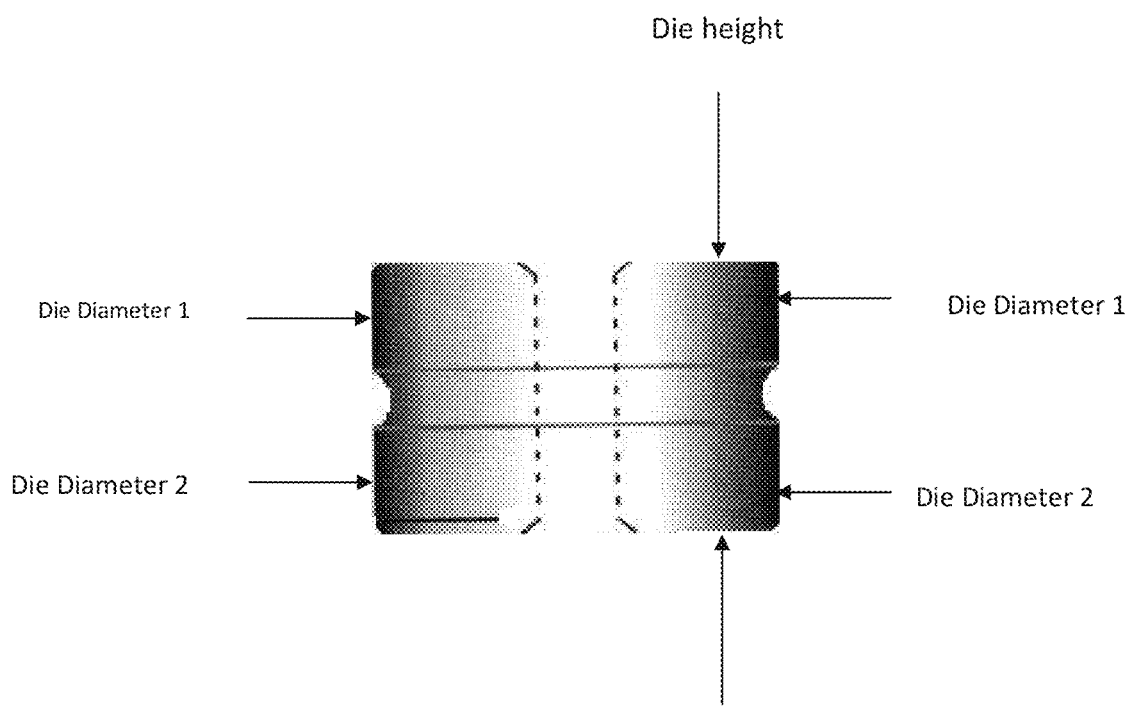
FIG. 5: illustrates an exemplary die along with various parameters to be inspected by the automated tablet tooling inspection system according to an embodiment of the present disclosure.

FIGS. 4(a), 4(b) and 5 depicts the various parameters inspected/measured during a preferred embodiment. FIG. 4(a) depicts punch barrel diameter 1 and punch barrel diameter 2. FIG. 4(b) depicts punch working length, the working length is the distance between bottom of the cup and the Head Flat. This is an important dimension and determines weight and thickness of the tablet. The distance between top of the cup and the head flat is called overall length as depicted. FIG. 5 depicts parameters inspected of a die in a preferred embodiment including but not limited to die diameter 1, die diameter 2 and die height.

Figure 6:
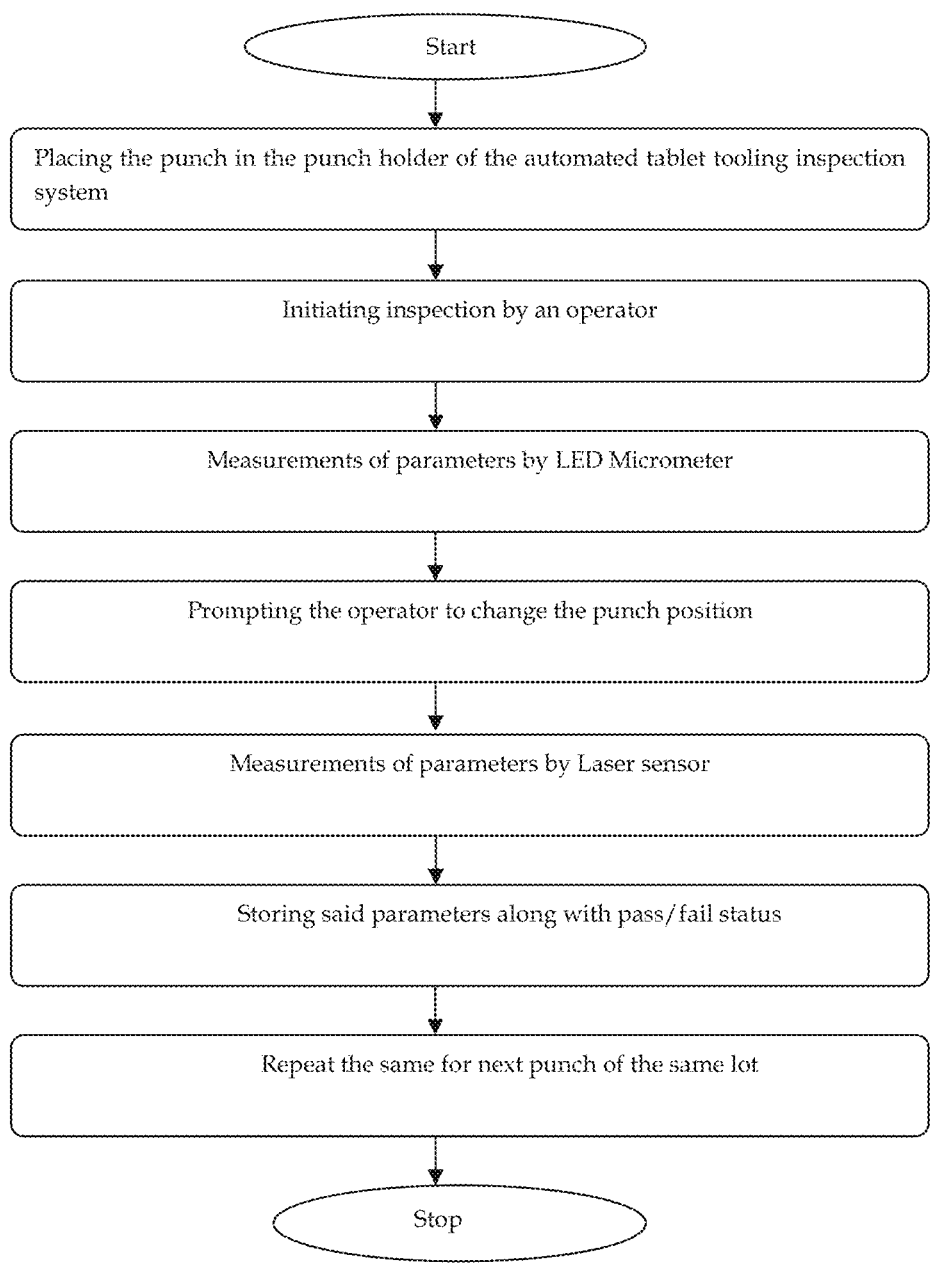
FIG. 6: illustrates a flow chart describing a method for inspection of a punch according to the present disclosure.
Figure 7:
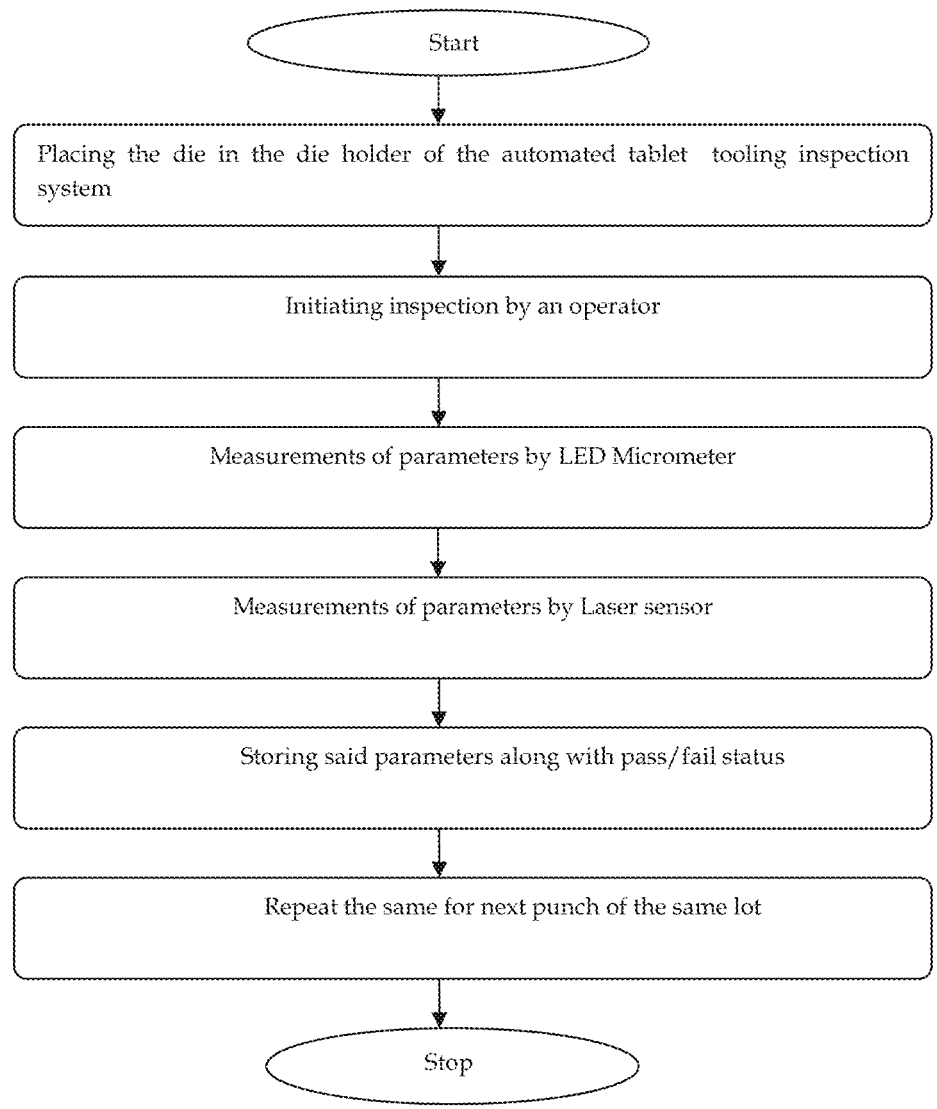
FIG. 7: illustrates a flow chart describing a method for inspection of a die according to the present disclosure.

FIG. 6 refers to a flowchart depicting the process of inspection to identify defects in a punch. Before initiating the process of punch inspection using the automated tablet tooling inspection system (100) the following two steps are performed as a prerequisite:

Adjusting the Laser sensor or con focal sensor (108): Every punch will have different cup shape. Hence the lowest point in the cup may be in the center or little away from the center. We need to adjust the sensor position to focus the beam exactly on the lowest point at least at one position during 360 deg rotation. The sensor is mounted on a dovetail, similar to a micrometer screw (Misumi make). This enables precision adjustment.

Calibrating the Laser sensor or con focal sensor (108): After adjusting the laser sensor or con focal sensor height, the sensor needs to be recalibrated to avoid the variation in reading due to position change, if any, in X axis. The measurement of working/overall length is based on calibrating the sensor based on a master punch which is validated for 133.60 mm length. The distance measured by sensor while measuring the master punch is stored in memory, say 2 mm. While measuring a new punch length, if the value measured now is 3 mm, then the actual working length is arrived as 133.60+(2−3) =132.60

Once the abovementioned steps are performed the punch to be inspected is placed in the punch holder (102) of the automated tablet tooling inspection system (100). The punch is placed with its tip facing the Laser sensor or con focal sensor (108) and its head touching punch stopper (103) of the automated tooling inspection system (100). The process of inspection is initiated by an operator through the graphical user interface of the control unit by providing instructions to the LED Micrometer (107) and Laser sensor or con focal sensor (108) of the system (100). LED Micrometer (107) measures parameter of the punch not limiting to punch barrel diameter 1, punch barrel diameter 2, punch barrel to tip concentricity and punch working length.

The automated tablet tooling inspection system (100) prompts the operator through audio/visual message on the graphical user interface of the control unit to change the punch position to place the punch with its head facing the Laser sensor or con focal sensor (108). Laser sensor or con focal sensor (108) of the system (100) measures parameters of the punch not limiting to punch overall length and punch cup depth. The parameters measured by LED Micrometer (107) and Laser sensor or con focal sensor (108) are stored in the storage device of the control unit as a report including the parameter measured along with a pass or fail status. The report stored can be viewed on the graphical user interface of said control unit.

The pass and fail status is determined on the basis of a predetermined tolerance limit. If the parameters are within the predetermined tolerance limit the status is stored as pass and if the parameters inspected are not within the predetermined tolerance limit they are stored as fail. The above mentioned steps are reiterated for inspection of another punch.

Figure 8:
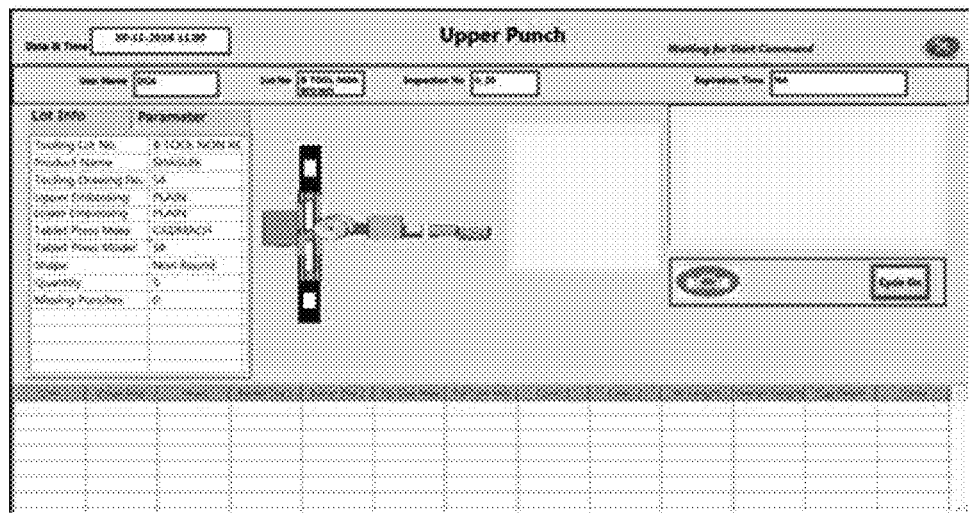
FIG. 8 shows an exemplary display on the graphical user interface of the control unit to initiate the process of present disclosure of a punch.

FIG. 8 refers to a flowchart depicting the process of inspection to identify defects in a die. The die to be inspected is placed in the die holder (104) of the automated tablet tooling inspection system (100). The inspection process is initiated by an operator through the graphical user interface of the control unit by providing instruction to the LED Micrometer (107) and Laser sensor or con focal sensor (108) of the system (100). LED Micrometer (107) measures parameters of the die not limiting to die diameter 1 and die diameter 2. Laser sensor or con focal sensor (104) of the system (100) measures parameter of the die not limiting to die height.

The parameters inspected by LED Micrometer (107) and Laser sensor or con focal sensor (108) are stored in the storage device of the control unit as a report including the parameter inspected along with a pass or fail status, wherein said inventory can be viewed on the graphical user interface of said control unit. The pass and fail status is determined on the basis of a predetermined tolerance limit. If the parameters are within the predetermined tolerance limit the status is stored as pass and if the parameters inspected are not within the predetermined limit the status is stored as fail. The above mentioned steps are reiterated for inspection of another die.

The present disclosure is further illustrated with the help of non limiting example.

EXAMPLE

Figure 9:
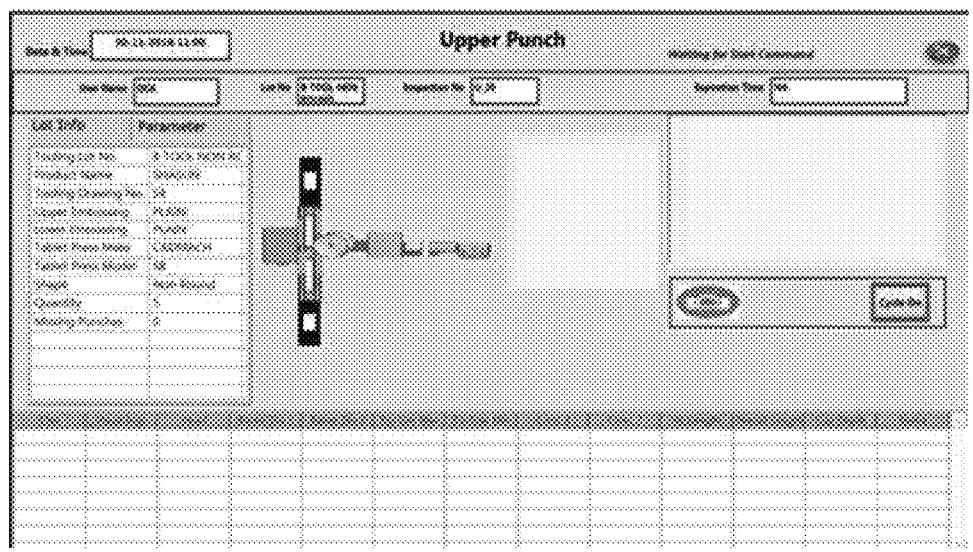
FIG. 9 shows an exemplary list of measured parameters and a pass/fail result for a punch.
Figure 10:
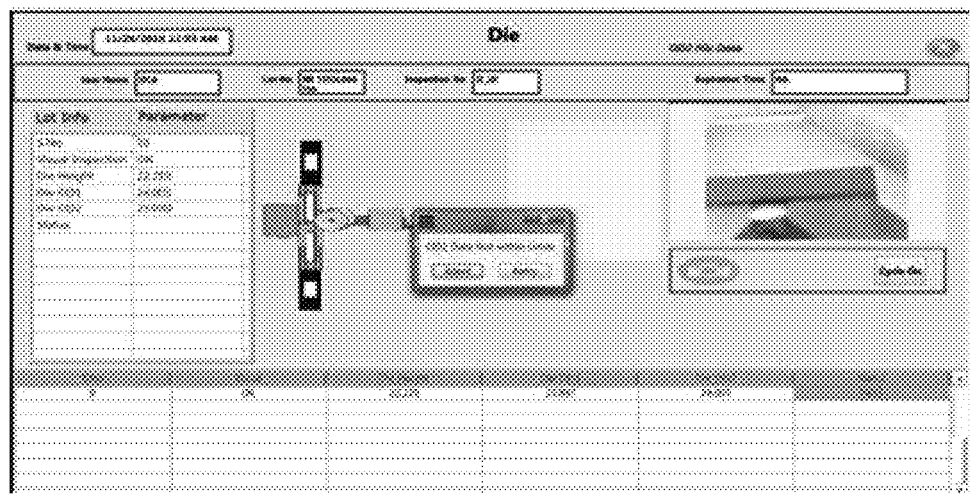
FIG. 10 shows a similar exemplary list of measured parameters and a pass/fail result for a die.
Figure 11:
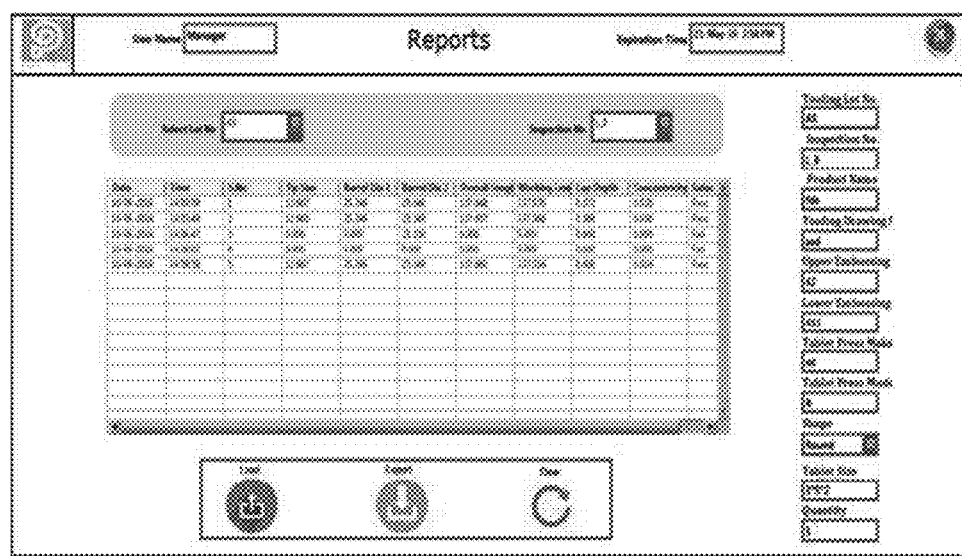
FIG. 11 shows an exemplary report.

An Automated tablet tooling inspection system (100) is generally used to inspect defects in different tablet tooling assemblies such as punches and dies. An operator/user places punch in the punch holder (102) if a punch is to be inspected and similarly a die to be inspected is placed in the die holder (104). Process of inspection is initiated by the operator through graphical user interface of control unit by providing commands to LED Micrometer (107) and Laser sensor or con focal sensor (108) of the automated tooling system (100). FIG. 8 shows an exemplary display on the graphical user interface of the control unit wherein the user/operator initiates the process of inspection of a upper punch by clicking on 'Cycle On'. The LED Micrometer (107) and Laser sensor or con focal sensor (108) measures parameters not limited to punch barrel diameter, punch tip maximum, punch tip minimum, punch barrel to tip concentricity, punch overall length, punch working length, punch tip cup depth, die outer dimension and die height. The parameters measured along with a pass/fail result are stored in storage device of the control unit as a report. FIG. 9 shows an exemplary list of measured parameters and a pass/fail result. FIG. 10 shows a similar exemplary list of measured parameters and a pass/fail result for a die. FIG. 11 shows an exemplary inventory.

I claim:

1. An automated tablet tooling inspection system for inspecting defects in tablet tooling including an upper punch, a lower punch and a die comprising:
    a base plate;
    a punch holder and a punch stopper adapted to hold punches, said punch holder fixed with said base plate;
    a die holder adapted to hold dies, said die holder fixed with said base plate;
    a LED micrometer fixed with a LM (linear motion) rail and carriage assembly to measure one or more first parameters of said tablet tooling, wherein said LM (linear motion) rail and carriage assembly fixed with said base plate;
    a Laser sensor or confocal sensor fixed with said base plate to measure one or more second parameters of said tablet tooling;
    a control unit comprising of a Graphical User Interface and a storage device adapted to receive instructions from an operator for initialing the process of inspecting defects in said tablet tooling, said initiation comprises sending commands to LED micrometer and Laser sensor or confocal sensor to inspect said at least one of the first and second parameters of said tablet tooling and storing said at least one of the first and second parameters along with a pass/fail status in the storage device as a report to reduce inspection time of said tablet tooling by minimizing manual intervention.

2. The automated tablet tooling inspection system as claimed in claim 1 wherein said manual intervention is reduced by eliminating the requirement of changing configuration of said system for inspection of any type of tablet tooling selected from the group comprising TSM/Euro, B, D, BD, BB and BBS.

3. The automated tablet tooling inspection system as claimed in claim 1 wherein said LED micrometer measures as the one or more first parameters at least one of punch barrel diameter, punch tip dimension, punch barrel to tip concentricity and die outer diameter.

4. The automated tablet tooling inspection system as claimed in claim 1 wherein said Laser sensor or confocal sensor measures as the one or more second parameters at least one of punch overall length, punch cup depth and die height.

5. The automated tooling inspection system as claimed in claim 1 wherein said punch barrel to tip concentricity is measured as one of the one or more first parameters in one single cycle along with the punch working length without any requirement of change in said system configuration thereby further reducing the inspection time.

6. The automated tooling inspection system as claimed in claim 1 wherein said storage device can be selected from a group of primary storage device, such as RAM, or a secondary storage device, such as a hard drive; wherein said secondary storage can be removable, internal, or external storage.

7. The automated tooling inspection system as claimed in claim 1 wherein said report comprises of said at least one of the first and second parameters inspected and a pass and fail status; wherein said pass/fail status is determined on the basis of a predetermined tolerance limit, if said at least one of the first and second parameters inspected are within the predetermined tolerance limit the status is stored as pass or else fail.

* * * * *